United States Patent [19]

Chang

[11] Patent Number: 5,290,743

[45] Date of Patent: Mar. 1, 1994

[54] PROCESS FOR REGENERATING A DEACTIVATED RHODIUM HYDROFORMYLATION CATALYST SYSTEM

[75] Inventor: Te Chang, West Chester, Pa.

[73] Assignee: Arco Chemical Technology L.P., Wilmington, Del.

[21] Appl. No.: 34,321

[22] Filed: Mar. 22, 1993

[51] Int. Cl.$^5$ ............... B01J 31/40; B01J 38/58; C07C 45/50
[52] U.S. Cl. .................... 502/30; 502/22; 502/24; 568/454
[58] Field of Search .............. 502/22, 23, 24, 30; 568/454

[56] References Cited

U.S. PATENT DOCUMENTS

| | | | |
|---|---|---|---|
| 3,555,098 | 1/1971 | Olivier et al. | 260/604 |
| 4,196,096 | 4/1980 | Dawes et al. | 252/414 |
| 4,215,077 | 7/1980 | Matsumoto et al. | 568/454 |
| 4,221,743 | 9/1980 | Halstead et al. | 568/454 |
| 4,297,239 | 10/1981 | Bryant et al. | 252/412 |
| 4,374,278 | 2/1983 | Bryant et al. | 568/454 |
| 4,400,547 | 8/1983 | Dawes et al. | 568/454 |
| 4,537,997 | 8/1985 | Kojima et al. | 568/454 |
| 4,605,780 | 8/1986 | Billig et al. | 568/454 |
| 4,861,918 | 8/1989 | Miller et al. | 568/454 |
| 4,935,550 | 6/1990 | Miller et al. | 502/30 |

FOREIGN PATENT DOCUMENTS

| | | | |
|---|---|---|---|
| 0495547 | 7/1992 | European Pat. Off. | 585/454 |
| 58-186443 | 10/1983 | Japan . | |
| 59-115752 | 7/1984 | Japan . | |
| 61-4534 | 1/1986 | Japan . | |
| 602219 | 3/1978 | U.S.S.R. | 502/24 |

Primary Examiner—Paul E. Konopka
Attorney, Agent, or Firm—Jonathan L. Schuchardt

[57] ABSTRACT

A process for regenerating a deactivated hydroformylation catalyst system that contains a rhodium hydridocarbonyl tris(trisubstituted phosphine) complex, a trisubstituted phosphine, and a diphosphinoalkane, is disclosed. The process involves oxidation of the catalyst system, removal of the phosphine oxidation products, and regeneration of the catalyst system by syngas treatment, aqueous extraction, and addition of phosphine ligands.

13 Claims, No Drawings

PROCESS FOR REGENERATING A DEACTIVATED RHODIUM HYDROFORMYLATION CATALYST SYSTEM

FIELD OF THE INVENTION

The invention relates to catalyst systems for hydroformylation of olefins. In particular, the invention is a process for regenerating a rhodium catalyst that has become partly inactive during its use in a hydroformylation process.

BACKGROUND OF THE INVENTION

Hydroformylation of olefins in the presence of rhodium complexes and trisubstituted phosphines is well known. The process is used commercially to manufacture n-butyraldehyde from propylene, and 4-hydroxybutanal from allyl alcohol. While rhodium catalysts are favored for their high activity, the catalysts deactivate over time and require regeneration or replacement. Because rhodium is so expensive, catalyst reactivation is needed to make the process commercially viable.

One way to prolong the lifetime of rhodium hydroformylation catalysts is to include a diphosphinoalkane in the catalyst system as is taught by Matsumoto et al. in U.S. Pat. No. 4,215,077. However, even when a diphosphinoalkane is used, catalyst lifetimes are shorter than desirable, and regeneration is needed.

Numerous processes have been suggested for reactivating rhodium hydroformylation catalysts. One process uses a distillation to concentrate rhodium catalyst residues, treats the residues with oxygen, and washes the catalyst system with water or aqueous base (see U.S. Pat. Nos. 4,297,239 and 4,374,278). In another process, the deactivated catalyst system is separated from the aldehyde products by extraction and is exposed to syngas (a gaseous mixture of hydrogen and carbon monoxide) to reactivate the catalyst (U.S. Pat. No. 4,537,997). In another process, the aldehyde content of the catalyst system is adjusted, the catalyst is then treated with an oxygen-containing gas, solid oxides are filtered out, and ligands (e.g., triphenylphosphine) are added to regenerate the catalyst (U.S. Pat. No. 4,196,096).

Although each of these processes has merit, none is satisfactory for regenerating catalyst systems that include a rhodium hydridocarbonyl tris(trisubstituted phosphine) complex, a trisubstituted phosphine, and a diphosphinoalkane. Simply treating the deactivated system with syngas is ineffective. Air oxidation of the system is helpful, but by itself, is inadequate. Aqueous washing of catalyst generates unwanted waste streams that require costly treatment and disposal. A process that allows reactivation and regeneration of these rhodium hydroformylation catalyst systems is needed. Especially desirable is a way of reactivating rhodium catalyst systems useful for allyl alcohol hydroformylation.

SUMMARY OF THE INVENTION

The invention is a process for regenerating a deactivated rhodium hydroformylation catalyst system that includes a rhodium hydridocarbonyl tris(trisubstituted phosphine), a trisubstituted phosphine, and a disphosphinoalkane. The process comprises reacting an organic solution of the catalyst system with an oxygen-containing gas to produce a solution of oxidized catalyst system that contains less than about 5 parts per million of residual diphosphinoalkane and less than about 100 parts per million of diphosphinoalkane monooxidation product. Following oxidation, phosphine oxidation products are removed from the organic solution by aqueous extraction, or by allowing solids to precipitate and separating the solids from the organic solution. Finally, the catalyst system is regenerated by exposing it to syngas, extracting the organic solution with water, and adding trisubstituted phosphine and diphosphinoalkane ligands.

Successful catalyst reactivation depends on thorough oxidation: if the diphosphinoalkane is not removed almost completely, reactivation will be ineffective. The sequence of steps in the process is important, although less critical than the degree of oxidation. A preferred ordering of steps is oxidation, removal of solid oxides from the oxidized solution, syngas treatment, aqueous extraction, and addition of phosphine ligands. The invention provides, for the first time, a practical way of regenerating a catalyst system based on a rhodium hydridocarbonyl tris(trisubstituted phosphine) complex, a trisubstituted phosphine, and a diphosphinoalkane.

DETAILED DESCRIPTION OF THE INVENTION

The hydroformylation catalyst system regenerated in the process of the invention includes a rhodium hydridocarbonyl tris(trisubstituted phosphine) complex, a trisubstituted phosphine, and a diphosphinoalkane.

Rhodium hydridocarbonyl tris(trisubstituted phosphine) complexes are well known in the art. These complexes have the general formula $HRh(CO)(PR_3)_3$ in which R is an alkyl, aryl, or aralkyl group. Suitable complexes include, but are not limited to, $HRh(CO)(PPh_3)_3$, $HRh(CO)(P(C_6H_4CH_3)_3)_3$, and the like. The triphenylphosphine complex is preferred.

An excess of trisubstituted phosphine is used in combination with the rhodium complex. Usually, the amount of trisubstituted phosphine used is within the range of about 10 to about 500 equivalents per equivalent of rhodium in the complex. Suitable trisubstituted phosphines include triarylphosphines, trialkylphosphines, alkyldiarylphosphines, triaryl phosphites, and the like. Examples include triphenylphosphine, tritolylphosphine, triphenylphosphite, propyldiphenylphosphine, and the like. Triphenylphosphine is preferred.

The catalyst system includes a diphosphinoalkane. The diphosphinoalkane has two phosphorus atoms joined together by an alkyl-substituted or unsubstituted alkylene radical having 2 to 5 carbons in the principal chain. Also attached to the phosphorus atoms are aryl or alkyl-substituted aryl groups such as phenyl or tolyl groups. Suitable examples are described fully in U.S. Pat. No. 4,215,077, the teachings of which are incorporated herein by reference in their entirety. Examples include, but are not limited to, bis(diphenylphosphino)ethane, bis(diphenylphosphino)butane, bis(ditolylphosphino)ethane, bis(ditolylphosphino)butane, and the like.

A solution of the catalyst system in an organic solvent is used for hydroformylation. Suitable organic solvents are those that can dissolve the rhodium complex, the trisubstituted phosphine, and the diphosphinoalkane and do not interfere with the hydroformylation reaction. Preferred organic solvents are aromatic and aliphatic hydrocarbons, ethers, ketones, and esters. Particularly preferred are aromatic hydrocarbons such as toluene.

The first step in the catalyst regeneration process of the invention involves oxidation of the deactivated catalyst system. An organic solution of the rhodium complex, trisubstituted phosphine, and diphosphinoalkane is reacted with an oxygen-containing gas. Any suitable oxygen-containing gas mixture can be used, including air and mixtures of air or oxygen with inert gases such as nitrogen and argon. For safety reasons, it is preferred to dilute the oxygen-containing gas mixture to an oxygen content that avoids the flammable limit for the particular organic solvent used. When toluene is used, for example, the oxygen content is diluted to less than about 11 volume percent. Preferred is a gaseous mixture containing from about 5 to about 7 volume percent oxygen in nitrogen.

The oxidation is performed under conditions effective to produce a solution of oxidized catalyst system that contains less than about 5 parts per million of residual diphosphinoalkane and less than about 100 ppm of diphosphinoalkane mono-oxidation product. Successful catalyst reactivation depends on thorough oxidation: if the diphosphinoalkane is not oxidized almost completely, catalyst reactivation will be ineffective. On the other hand, prolonged oxidation gives little or no additional benefit. The diphosphinoalkane oxidizes more easily than the trisubstituted phosphine. Generally, at the completion of the oxidation of the diphosphinoalkane, the oxidized solution of catalyst system will contain less than about 2 wt. % of trisubstituted phosphine oxide. There is no apparent benefit to further oxidizing the trisubstituted phosphine, provided that the diphosphinoalkane content is reduced to less than about 5 ppm. The oxidation can be performed over a wide temperature range. A preferred range is from about 20° C. to about 100° C.; more preferred is the range from about 45° C. to about 80° C. Most preferred is the range from about 55° C. to about 70° C.

Generally, the oxidation will be most conveniently performed by sparging the oxygen-containing gas through the organic solution containing the deactivated catalyst over a period of several hours. Periodic analysis of the solution gives a measure of the residual diphosphinoalkane and diphosphinoalkane mono-oxidation product. Usually, the catalyst reactivation procedure can be completed within about 24 hours.

After the oxidation is complete, phosphine oxidation products are removed from the organic solution. Removal of the phosphine oxidation products can be accomplished by extracting the organic solution with water and/or a dilute solution of aqueous base. When a wash with aqueous base is used, it will generally be followed by a water wash to remove any residual base from the washed organic solution. A disadvantage of aqueous washing to remove phosphine oxidation products is that some of the rhodium (up to about 2 wt. %) is lost to the aqueous stream. In addition, substantial amounts of aqueous and solid wastes requiring costly treatment and disposal are generated.

A more preferred method of removing the phosphine oxidation products is to allow solids to precipitate from the oxidized catalyst system, and to separate the solids from the organic solution. The separation can be achieved by any suitable method, including, for example, filtration, centrifugation, decanting, or the like. Filtration is preferred. The solids will contain mostly mono- and dioxides of the diphosphinoalkane, and a minor amount of trisubstituted phosphine oxide. Complete precipitation may require hours or even days. Preferably, the mixture is allowed to settle for at least about 2 days. The precipitation process can be accelerated if desired by sparging syngas or an inert gas through the solution, or by adding a nucleating agent such as a diphosphinoalkane dioxide.

Filtration is preferably used to remove solids from the solution of oxidized catalyst system. Any filtration technique capable of removing fine particles from a liquid can be used. Generally, it is preferred to use a filtration technique capable of removing particles of 2 $\mu$m diameter. The isolated solids will contain a small proportion (usually about 1 wt. %) of rhodium, which can be reclaimed by any suitable technique, such as ashing of the solids.

After the phosphine oxidation products have been removed either by aqueous extraction or by removing precipitated solids, the catalyst system is regenerated. The catalyst system is exposed to syngas, water extraction, and addition of trisubstituted phosphine and diphosphinoalkane ligands to regenerate the catalyst system. The order in which these steps are performed is not critical. However, the preferred order involves syngas treatment, followed by water extraction, followed by addition of phosphine ligands. Syngas treatment is performed before water extraction to minimize losses of rhodium to the aqueous phase during extraction. Reactivation is also most successful when addition of the phosphine ligands follows exposure of the oxidized catalyst system to syngas.

The syngas conditioning is typically performed by sparging carbon monoxide and hydrogen through the oxidized catalyst solution. In a preferred process, the syngas treatment is first performed for at least about 2 hours on the organic solution, and is then continued with a coincidental water extraction of the solution.

The trisubstituted phosphine and diphosphinoalkane are typically added in amounts effective to restore the catalyst system to its original design composition, although any suitable amount can be added. Generally, the catalyst will have poor activity unless the proper amount of diphosphinoalkane is added.

The following examples merely illustrate the invention; those skilled in the art will recognize numerous variations that are within the spirit of the invention and scope of the claims.

Hydroformylation Procedure A

Rhodium catalyst activities before and after catalyst regeneration are found by measuring the first-order rate constant for allyl alcohol consumption in a continuous hydroformylation pilot unit. Activities are measured at about the same phosphine concentrations for a reasonable comparison of rates.

The continuous hydroformylation pilot unit consists of a continuous stirred-tank reactor (CSTR), a plug-flow reactor (PFR), and a water extraction column. A partially deactivated catalyst sample from a hydroformylation process is used. The catalyst solution contains 180 ppm rhodium, triphenylphosphine (about 7 wt. %), and 1,4-bis(diphenylphosphino)butane (about 250 ppm) in toluene.

The volumetric ratio of allyl alcohol to catalyst solution fed into the CSTR is about 0.16. Hydroformylation is performed in the CSTR at 140° F. and 20 psig with syngas sparged at a $H_2/CO$ ratio of 4.4. Hydroformylation continues in the PFR, the aldehyde reaction products are extracted into water in the column, and the toluene solution of catalyst is recycled to the CSTR. The first-order rate constant for allyl alcohol consumption at 140° F. is 1.6 $h^{-1}$.

EXAMPLE 1

CATALYST REGENERATION BY OXIDATION EFFECT OF COMPLETE VERSUS INCOMPLETE DIPHOSPHINOALKANE OXIDATION

Part (a)—Incomplete Oxidation

The hydroformylation procedure of Procedure A is stopped, and the catalyst solution is drained from the CSTR. The catalyst solution is sparged with a mixture of nitrogen and air (5% oxygen content) at 70° F. and atmospheric pressure in a batch reactor for 48 h. Analysis of the oxidized catalyst solution indicates that 0.35 wt. % of the triphenylphosphine (TPP) is converted to triphenylphosphine oxide (TPPO), and the residual concentrations of 1,4-bis(diphenylphosphino)butane (DPB) and the mono-oxide of DPB (DPBO) are 8 ppm and 190 ppm, respectively.

The oxidized catalyst solution is filtered to remove precipitated solids from the solution, and is returned to the hydroformylation unit. The catalyst solution is circulated through the continuous unit with syngas conditioning, water extraction, and adjustment of phosphine ligands before beginning hydroformylation of more allyl alcohol. The first-order rate constant measured at 140° F. is 1.7 $h^{-1}$, which suggests little or no improvement in catalyst activity as a result of this reactivation procedure.

Part (b)—Complete Oxidation

The catalyst solution from Part (a) is drained from the CSTR, and is again sparged with a mixture of nitrogen and air (5% oxygen), this time at 150° F. and 50 psig for 24 h. Analysis of the oxidized solution indicates that 0.9 wt. % of the TPP is converted to TPPO, and the residual concentrations of DPB and DPBO are <5 ppm and 39 ppm, respectively.

The oxidized catalyst solution is filtered and returned to the hydroformylation unit. The sequence of syngas conditioning, water extraction, and phosphine ligand adjustment is repeated as described in Part (a) prior to beginning allyl alcohol addition. The rate constant measured at 140° F. is 2.6 $h^{-1}$.

The critical difference between the reactivated catalyst solutions in Parts (a) and (b) is in the degree of oxidation of the phosphines: at 8 ppm residual DPB and 190 ppm residual DPBO, catalyst reactivation is insignificant; more complete oxidation of DPB to <5 ppm and DPBO to 39 ppm effectively reactivates the catalyst.

EXAMPLE 2

EFFECT OF SYNGAS TREATMENT ON CATALYST REACTIVATION

Part (a)—Without Oxidation

A partially deactivated hydroformylation catalyst sample containing 140 ppm of rhodium, 5.5 wt. % of triphenylphosphine, and 250 ppm of DPB in toluene is treated with syngas ($H_2/CO=3$) at 150° F. and 65 psig in a batch reactor for 29 h.

The syngas-treated catalyst solution is tested in the continuous hydroformylation pilot unit as described in Procedure A. The rate constant measured at 140° F. before and after the syngas treatment is the same: 1.4 $h^{-1}$.

Part (b)—With Oxidation

A sample of the catalyst solution from Part (a) is exposed to air at room temperature and atmospheric pressure for 2 days, and is then treated with syngas ($H_2/CO=4$) at 150° F. and 250 psig for 24 h. The allyl alcohol consumption rate constant improves to 1.9 $h^{-1}$. The catalyst solution in the continuous pilot unit is treated with air/nitrogen (1:1) mixture at 150° F. and 20 psig for 4 h. Analysis indicates that the oxidized solution contains 4 ppm of DPB and 94 ppm of DPBO, and about 0.5 wt. % of the TPP is oxidized to TPPO. After adjusting the levels of phosphine ligands, the rate constant for allyl alcohol consumption at 140° F. improves to 2.2 $h^{-1}$.

This example shows that syngas treatment alone is ineffective in reactivating the catalyst, and that oxidation is required.

EXAMPLE 3

EFFECT OF AIR EXPOSURE

Another sample of deactivated hydroformylation catalyst solution (same sample used in Example 2) is exposed to air for two months in a half-filled container. Analysis of the air-exposed catalyst indicates that it contains 6 ppm of DPB and 19 ppm of DPBO; the TPP concentration is 0.5 wt. % less than that of a fresh sample. The catalyst sample is tested in the pilot-scale continuous hydroformylation unit as described in Procedure A. The DPB level is adjusted after syngas conditioning, water extraction, and start of the allyl alcohol. The rate constant for allyl alcohol consumption at 140° F. is 2.2 $h^{-1}$, which is comparable to the activity of the catalyst solution that is purposefully exposed to oxygen (See Example 1(b)). Catalyst activity improves from a rate constant of 1.4 $h^{-1}$ for the unoxidized sample.

EXAMPLE 4

EFFECT OF PREMATURE EXPOSURE OF REACTIVATED CATALYST TO PHOSPHINE LIGANDS

The air-exposed catalyst sample of Example 3 is mixed with DPB (190 ppm), and is tested in the pilot-scale hydroformylation unit. The initial rate of allyl alcohol consumption is 1.2 at 140° F., but gradually increases to 1.8 in 3 days. This example shows that phosphine adjustment is preferably performed after the oxidized catalyst solution has been exposed to syngas conditioning and water extraction.

The preceding examples are meant as illustrations; the boundaries of the invention are defined by the following claims.

I claim:

1. A process for regenerating a deactivated rhodium hydroformylation catalyst system that includes a rhodium hydridocarbonyl tris(trisubstituted phosphine) complex, a trisubstituted phosphine, and a diphosphinoalkane, said process comprising:
   (a) isolating an organic solution containing the deactivated catalyst system from an olefin hydroformylation process by separating the organic solution from an aqueous extract of aldehyde reaction products;
   (b) reacting the organic solution with an oxygen-containing gas at a temperature and for a time effective to produce a solution of oxidized catalyst system that contains less than about 5 parts per million of residual diphosphinoalkane and less than about 100 parts per million of diphosphinoalkane mono-oxidation products;

(c) removing phosphine oxidation products from the organic solution by allowing solids to precipitate and separating the solids from the organic solution; and (d) exposing the organic solution to syngas, extracting it with water, and adding trisubstituted phosphine and diphosphinoalkane ligands in a manner and in amounts effective to form a regenerated catalyst system that has enhanced catalytic activity for hydroformylation of olefins to aldehydes compared with the deactivated catalyst system.

2. The process of claim 1 wherein the solution of oxidized catalyst system contains less than about 2 wt. % of trisubstituted phosphine oxide.

3. The process of claim 1 wherein phosphine oxidation products are removed from the organic solution by allowing solids to precipitate, and filtering the solids from the solution.

4. The process of claim 1 wherein the trisubstituted phosphine is selected from the group consisting of triaryl phosphines, triaryl phosphites, and alkyldiarylphosphines.

5. The process of claim 1 wherein the diphosphinoalkane is selected from the group consisting of bis-diphenylphosphino)ethane, bis(diphenylphosphino)butane, bis(ditolylphosphino)ethane, and bis(ditolylphosphino)butane.

6. The process of claim 3 wherein the catalyst system is regenerated by exposing the filtered organic solution of catalyst system to syngas, followed by extracting the solution with water, followed by adding trisubstituted phosphine and diphosphinoalkane ligands.

7. The process of claim 1 wherein the oxidation is performed at a temperature within the range of about 20° C. to about 100° C.

8. The process of claim 1 wherein the oxidant is a gaseous mixture of nitrogen and oxygen that has an oxygen content within the range of about 5 to about 7 volume percent.

9. A process for regenerating a deactivated rhodium hydroformylation catalyst system that includes a rhodium hydridocarbonyl tris(trisubstituted phosphine) complex, a trisubstitued phosphine, and a diphosphinoalkane, said process comprising:

(a) isolating an organic solution containing the deactivated catalyst system from an olefin hydroformylation process by separating the organic solution from an aqueous extract of aldehyde reaction products;

(b) reacting the organic solution with an oxygen-containing gas at a temperature and for a time effective to produce a solution of oxidized catalyst system that contains less than about 5 parts per million of residual diphosphinoalkane and less than about 100 parts per million of diphosphinoalkane mono-oxidation products;

(c) removing phosphine oxidation products from the organic solution by aqueous extraction; and (d) exposing the organic solution to syngas, extracting it with water, and adding trisubstituted phosphine and diphosphinoalkane ligands in a manner and in amounts effective to form a regenerated catalyst system that has enhanced catalytic activity for hydroformylation of olefins to aldehydes compared with the deactivated catalyst system.

10. The process of claim 9 wherein the solution of oxidized catalyst system contains less than about 2 wt. % of triphenylphosphine oxide.

11. The process of claim 9 wherein the diphosphinoalkane is selected from the group consisting of bis(diphenylphosphino)ethane, bis(diphenylphosphino)butane, bis(ditolylphosphino)ethane, and bis(ditolylphosphino)butane.

12. The process of claim 9 wherein oxidation is performed at a temperature within the range of about 20° C. to about 100° C.

13. A process for regenerating a deactivated rhodium hydroformylation catalyst system that includes a rhodium hydridocarbonyl tris(trisubstitued phosphine) complex, a trisubstituted phosphine, and a diphosphinoalkane, said process comprising:

(a) isolating an organic solution containing the deactivated catalyst system from an olefin hydroformylation process by separating the organic solution from an aqueous extract of aldehyde reaction products;

(b) reacting the organic solution with a gaseous mixture of nitrogen and oxygen that has an oxygen content within the range of about 5 to about 7 volume percent, at a temperature and for a time effective to produce a solution of oxidized catalyst system that contains less than about 5 parts per million of residual diphosphinoalkane and less than about 100 parts per million of diphosphinoalkane mono-oxidation products;

(c) allowing solids to precipitate from the organic solution of oxidized catalyst system;

(d) filtering the organic solution to remove the solids;

(e) exposing the organic solution to syngas;

(f) washing the organic solution with water; and (g) adding trisubstituted phosphine and diphosphinoalkane ligands in amounts effective to form a regenerated catalyst system that has enhanced catalytic activity for hydroformylation of olefins to aldehydes compared with the deactivated catalyst system.

* * * * *